United States Patent [19]
Krueger et al.

[11] Patent Number: 5,254,378
[45] Date of Patent: * Oct. 19, 1993

[54] RADIATION RESISTANT POLYPROPYLENE ARTICLES AND METHOD FOR PREPARING SAME

[75] Inventors: Dennis L. Krueger, Hudson, Wis.; Thomas I. Insley, Lake Elmo, Minn.; Daniel E. Meyer, Stillwater, Minn.; Richard J. Rolando, Oakdale, Minn.

[73] Assignee: Minnesota Mining and Manufacturing Company, St. Paul, Minn.

[*] Notice: The portion of the term of this patent subsequent to Jan. 7, 2009 has been disclaimed.

[21] Appl. No.: 869,072

[22] Filed: Apr. 6, 1992

Related U.S. Application Data

[60] Continuation of Ser. No. 486,083, Feb. 27, 1990, abandoned, which is a division of Ser. No. 302,126, Jan. 24, 1989, Pat. No. 4,931,230, which is a continuation of Ser. No. 43,094, Apr. 30, 1987, abandoned, which is a continuation-in-part of Ser. No. 861,068, May 8, 1986, abandoned.

[51] Int. Cl.$^5$ .................................................. C08J 3/28
[52] U.S. Cl. .................................... 428/34.1; 428/35.7; 428/36.92; 428/500; 522/157; 526/348.1; 526/351; 206/524.4
[58] Field of Search .................... 526/348.1, 351, 936; 206/524.1, 524.4; 428/35.7, 36.92, 221, 224, 292, 365, 500, 903, 910, 34.1, 35.2, 288, 1; 522/157; 525/333.7

[56] References Cited

U.S. PATENT DOCUMENTS

| | | | |
|---|---|---|---|
| 3,987,001 | 10/1976 | Wedel et al. | 260/32.8 |
| 4,110,185 | 8/1978 | Williams et al. | 304/159 |
| 4,113,595 | 9/1978 | Hagiwara et al. | 204/159 |
| 4,274,932 | 6/1981 | Williams et al. | 204/159 |
| 4,431,497 | 2/1984 | Rekers | 204/159 |
| 4,460,445 | 7/1984 | Rekers | 204/159 |
| 4,467,065 | 8/1984 | Williams et al. | 524/296 |
| 4,739,025 | 4/1988 | Krueger | 526/348.1 |
| 4,950,549 | 8/1990 | Rolando et al. | 428/500 |
| 5,078,925 | 1/1992 | Rolando et al. | 264/6 |

FOREIGN PATENT DOCUMENTS 0068555 5/1983 European Pat. Off. .
0154071 11/1985 European Pat. Off. .

OTHER PUBLICATIONS

(Natta, G., et al., Structure and Properties of Isotactic Polypropylene, *Del Nuovo Cimento*, Suppl. Al, vol. XV, Serie X, N.1, 1960, pp. 40–51.
(Pimer, S. H., ed., *Weathering and Degradation of Plastics*, Gordon & Breach, Science Publishers Inc., N.Y., 1966, pp. 104–107).
P. H. Geil *Polymer Single Crystals*, Interscience, N.Y., 1963, p. 270.
R. L. Miller *On the Existence of Near-Range Order in Isotactic Polypropylenes*, Polymer, 1, 135 (1960).
Report No. 4364 of the Naval Research Laboratories, published May 25, 1954 *Manufacture of Superfine Organic Fibers*, by Wente, Van A. et al.
Wente, Van A., *Superfine Thermoplastic Fibers*, Industrial Engineering Chemistry, vol. 48, No. 8, Aug. 1956, pp. 1342–1346.

*Primary Examiner*—Ellis P. Robinson
*Assistant Examiner*—Charles R. Nold
*Attorney, Agent, or Firm*—Griswold, Gary L.; Walter N. Kirn; Carole Truesdale

[57] ABSTRACT

Irradiated polypropylene articles of non-crystalline mesomorphous polypropylene and a method for preparing the articles are provided. The articles are irradiated with a sterilizing dosage of ionizing radiation. The irradiated articles such as films and blown microfiber webs are substantially undegraded after storage periods of as long as six months.

9 Claims, 4 Drawing Sheets

RADIATION RESISTANT POLYPROPYLENE ARTICLES AND METHOD FOR PREPARING SAME

This application is a continuation of application Ser. No. 07/486,083, filed Feb. 27, 1990, now abandoned which is a division of application Ser. No. 07/302,126, filed Jan. 24, 1989, U.S. Pat. No. 4,931,230 which is a continuation of application Ser. No. 07/043,094, filed Apr. 30, 1987, now abandoned which is a continuation-in-part of application Ser. No. 06/861,068, filed May 8, 1986, now abandoned.

BACKGROUND OF THE INVENTION

1. Field of the Invention

This invention relates to irradiated polypropylene articles, such as fibers, films, and nonwoven fabrics and to a method for preparing such articles.

2. Background Information

Polypropylene is often a material of choice for articles of medical use due to its various properties such as non-toxicity and inertness to drugs and liquid media used with drugs, as well as its low cost and the ease with which it can be extruded, molded, and formed into articles. Such articles generally require sterilization before use. A preferred method of sterilization is by gamma radiation using radioactive cobalt since it can be performed on impermeably wrapped packages ensuring total and reliable sterility. However, gamma-irradiated polypropylene is subject to degradation, e.g., embrittlement, discoloration, and thermal sensitivity, during or subsequent to irradiation.

The addition of various stabilizers, e.g., antioxidants, to the polypropylene material has been suggested to prevent discoloration and degradation.

U.S. Pat. No. 4,110,185 (Williams et al.) discloses irradiation sterilized articles of polypropylene which have incorporated therein a mobilizer which increases the free volume of the polymer and, therefore, lowers the density of the polymer. Suitable mobilizers mentioned include hydrocarbon oils, halogenated hydrocarbon oils, phthalic ester oils, vegetable oils, silicone oils, and polymer greases.

U.S. Pat. No. 4,113,595 (Hagiwara et al.) discloses irradiated crosslinked polyolefin molded products of a blend of polyolefin, a compound having acetylenic linkage, and an aromatic hydrocarbon-substituted organic amine or an aromatic secondary amino compound.

U.S. Pat. Nos. 4,274,932 and 4,467,065 (Williams et al.) disclose polypropylene stabilized for irradiation sterilization. The polypropylene has a narrow molecular weight distribution and has incorporated therein a mobilizer, as used in U.S. Pat. No. 4,110,185, described hereinabove.

U.S. Pat. No. 4,431,497 (Rekers) discloses radiation-stable polyolefin compositions containing a benzhydrol or benzhydrol derivative stabilizer.

U.S. Pat. No. 4,460,445 (Rekers) discloses radiation-stable polyolefin compositions containing a hindered phenolic stabilizer and a benzaldehyde acetal stabilizer.

European Patent Application No. 0,068,555 (Lenzi) discloses irradiation-sterilizable polypropylene articles, the polypropylene having one to eight weight percent low density polyethylene added thereto.

U.S. Pat. No. 3,987,001 (Wedel et al.) discloses an ultraviolet protectorant composition for surface application by aerosol to polyolefins, which composition contains a 2-hydroxy benzophenone and benzoate ester ultraviolet protectorant, a polymethacrylate binder, a solvent, and propellant.

Although the addition of the various stabilizers to polypropylene serves to diminish degradation by radiation, the use of additives increases costs, some additives may pose toxicological problems when contacted with pharmaceuticals, and some additives may adversely affect the physical properties of the polypropylene.

The present invention overcomes these problems without addition of radiation stabilizing additives as required in the aforementioned Williams et al. '195, '932 and '065, Hagiwara et al. '595, Rekers '497 and '445, Lenzi '555, and Wedel '001 patents, and provides low cost irradiated polypropylene articles and a method for preparing irradiated polypropylene articles, with the articles exhibiting little or no degradation after irradiation even after prolonged storage periods.

SUMMARY OF THE INVENTION

The present invention provides irradiated polypropylene articles of non-crystalline mesomorphous polypropylene, which polypropylene need not contain radiation stabilizing additives, the articles having been irradiated with a sterilizing dosage of ionizing radiation. The irradiated articles such as films and blown microfiber webs are substantially undegraded after storage periods of as long as six months. For example, films of the invention generally retain an elongation at break of at least 200 percent, preferably at least 300 percent, after irradiation, and blown microfiber webs and other articles retain at least 50 percent, preferably at least 80 percent, of the elongation at break that they exhibited prior to irradiation.

The invention further provides a method for preparing irradiated polypropylene articles, the steps of which include: extruding polypropylene which polypropylene need not contain radiation stabilizing additives; quenching the extruded polypropylene immediately after extrusion to provide non-crystalline mesomorphous polypropylene; and irradiating the non-crystalline mesomorphous polypropylene with a dosage of ionizing radiation that would degrade crystalline polypropylene. The irradiated articles, after six months storage, are substantially undegraded.

Although non-crystalline, mesomorphous polypropylene is known (Natta, G., et al. Structure and Properties of Isotactic Polypropylene, *Del Nuovo Cimento* Supplemento Al, Volume XV, Serie X, N.1, 1960, pp. 40–51) the present invention for the first time, insofar as known, applies a sterilizing dose of gamma radiation to non-crystalline, mesomorphous polypropylene to achieve non-degraded gamma radiation-sterilized polypropylene products. In fact, it has been thought that crystalline regions in polypropylene provide oxygen-impermeable regions which limit the extent of oxidation and reduce the maximum oxidation rate, and that readily-accessible amorphous regions were preferentially attacked (Pimer, S.H., ed., *Weathering and Degradation of Plastics*, Gordon and Breach, Science Publishers Inc., New York, 1966, pp. 104–107).

It is suspected that the radiation stability of the non-crystalline mesomorphous polypropylene is related to control of the morphology. The non-crystalline mesomorphous polypropylene has been described as a non-spherulitic structure by P.H. Geil (*Polymer Single Crystals*, Interscience, N.Y., 1963, p. 270). Crystalline polypropylene may have "chain-folds", i.e., crystalline/amorphous folds, in the structure which provide areas for radical attack because of their higher energy. In contrast, the non-crystalline mesomorphous structure is believed to have ordering as in a Fringed Micelle model with no chain-fold defects. It is suspected that this lack of chain fold defects minimizes the number of sites for radical attack and thereby provides the resistance to radiation degradation.

DETAILED DESCRIPTION OF THE INVENTION

Polypropylene to be used in products of the invention can be extruded from polymer melt in any shape which can be rapidly cooled throughout after extrusion to obtain non-crystalline mesomorphous phase polypropylene. The shape and/or thickness of the extruded material will be dependent on the efficiency of the quenching systems utilized. Generally, films, and blown microfiber webs are the preferred extruded materials. The extruded polypropylene should not be subjected to any treatment at temperatures above about 140° F (60° C), such as orientation or stretching, as such treatment would change the polypropylene structure to the crystalline phase. After irradiation, the polypropylene can be stretched or oriented if properties provided by such treatment are desired.

The polypropylene may contain conventional additives such as antistatic materials, dyes, plasticizers, ultraviolet absorbers, nucleating agents and the like. The amount of additives is typically less than ten weight percent of the polymer component, preferably less than two percent by weight.

Figure 2:
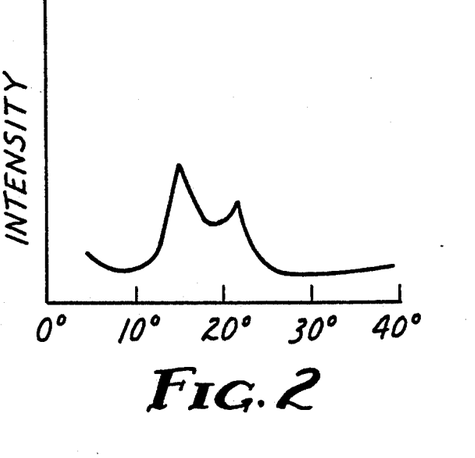
FIG. 2 is the X-ray diffraction pattern of the non-crystalline mesomorphous polypropylene film of Example 2.
Figure 3:
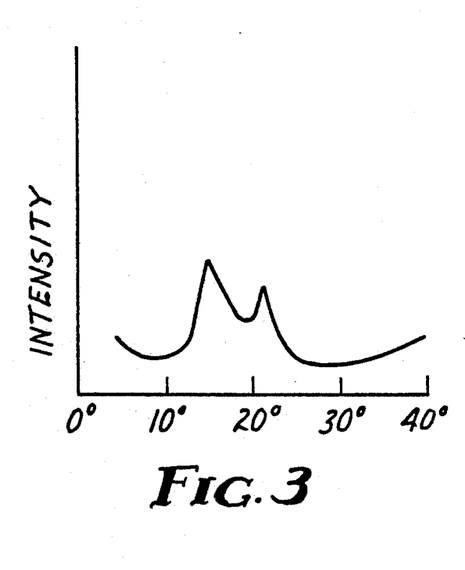
FIG. 3 is the X-ray diffraction pattern of the non-crystalline mesomorphous polypropylene film of Example 3.
Figure 4:
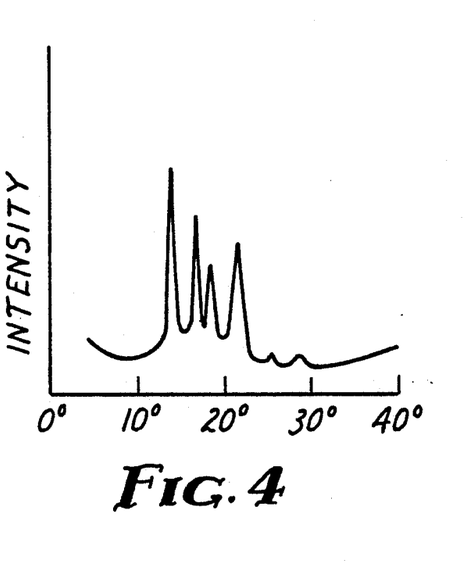
FIG. 4 is the X-ray diffraction pattern of the crystalline polypropylene film of Comparative Example 1.
Figure 6:
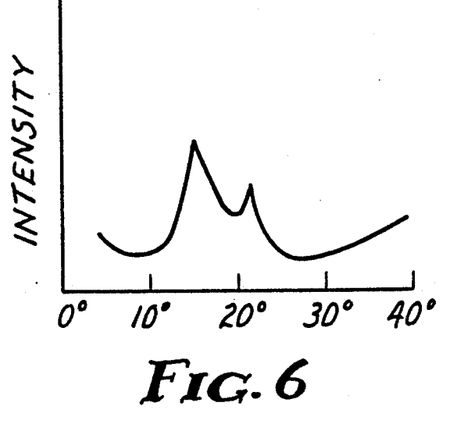
FIG. 6 is the X-ray diffraction pattern of the non-crystalline polypropylene film of Example 5.
Figure 7:
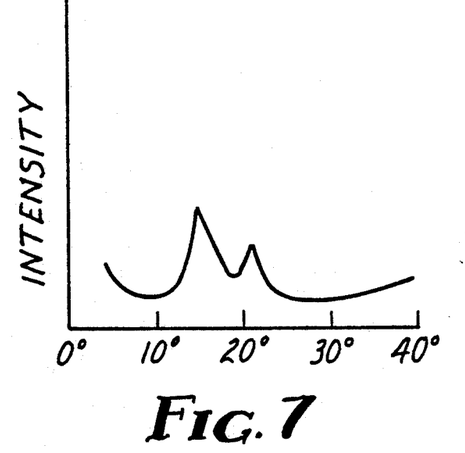
FIG. 7 is the X-ray diffraction pattern of the non-crystalline mesomorphous polypropylene film of Example 6.
Figure 8:
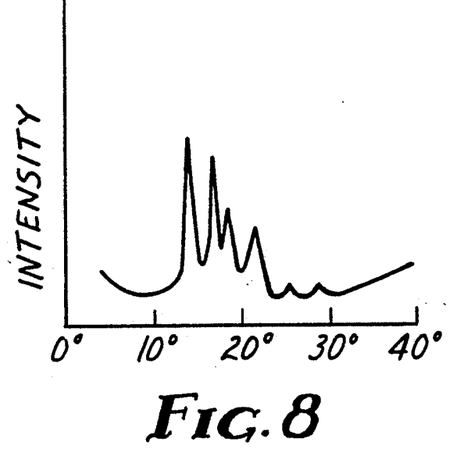
FIG. 8 is the X-ray diffraction pattern of the crystalline polypropylene film of Comparative Example 2.
Figure 10:
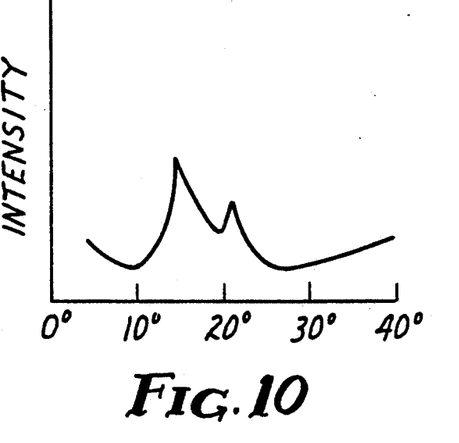
FIG. 10 is the X-ray diffraction pattern of the non-crystalline mesomorphous polypropylene film of Example 8.
Figure 11:
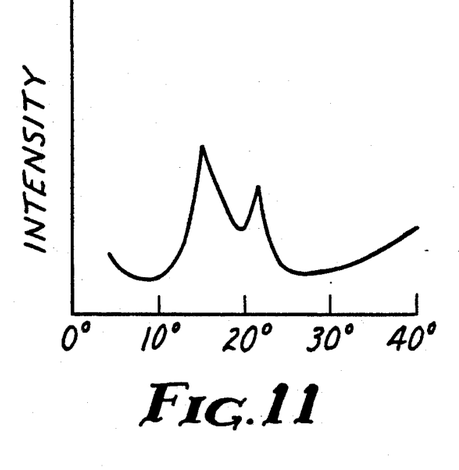
FIG. 11 is the X-ray diffraction pattern of the non-crystalline mesomorphous polypropylene film of Example 9.
Figure 12:
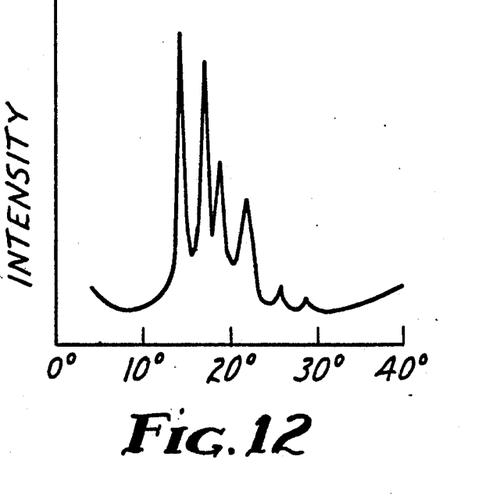
FIG. 12 is the X-ray diffraction pattern of the crystalline polypropylene film of Comparative Example 3.

To obtain the non-crystalline mesomorphous phase polypropylene, the extruded material must be quenched immediately after extrusion before the material reaches the crystalline state. The presence of the non-crystalline mesomorphous phase polypropylene can be confirmed by X-ray diffraction. FIGS. 1-3, 5-7, 9-11, and 13 are X-ray diffraction patterns for non-crystalline mesomorphous polypropylene. FIGS. 4, 8 and 12 are X-ray diffraction patterns for crystalline polypropylene. Although the term "non-crystalline mesomorphous" is used to describe the polypropylene useful in the present invention, the material contains some crystalline phase polypropylene as determined by density measurements using a gradient column. Generally, the percent crystallinity of the non-crystalline mesomorphous polypropylene is below about 45 percent.

Various known methods of quenching can be used to obtain the non-crystalline mesomorphous structure including plunging the extruded material into a cold liquid, e.g., ice water bath, spraying the extruded material with a liquid such as water, and/or running the extruded material over a cooled roll or drum.

Extruded polypropylene film is preferably quenched by contact with a quench roll or by plunging the film into a quench bath, such as an ice-water bath as disclosed by R. L. Miller ("On the Existence of Near-range Order in Isotactic Polypropylenes", *Polymer*, 1, 135 (1960). Where a quench roll is used, the roll temperature is preferably maintained at a temperature below about 75° F. (24° C.) and the film is generally in contact with the roll until solidified. The quench roll should be positioned relatively close to the extruder die, the distance being dependent on the roll temperature, the extrusion rate, the film thickness, and the roll speed. Generally, the distance from the die to the roll is about 0.1 in (0.25 cm) to 2 in (5 cm). Where a quench bath is used, the bath temperature is preferably maintained at a temperature below about 40° F. (4° C.). The bath should be positioned relatively close to the die, generally about 0.1 in (0.25 cm) to 5 in (13 cm) from the die to the bath.

Polypropylene melt blown microfibers are produced by extruding molten polymer through a die into a high velocity hot air stream to produce fibers having an average fiber diameter of less than about 10 microns. The fibers are generally collected on a drum in the form of a web. The preparation of microfiber webs is described in Report No. 4364 of the Naval Research Laboratories, published May 25, 1954, entitled "Manufacture of Superfine Organic Fibers," by Wente, Van A. et al. and in Wente, Van A., "Superfine Thermoplastic Fibers" in *Industrial Engineering Chemistry*, Vol. 48, No. 8, August, 1956, pp. 1342-1346. To achieve non-crystalline, mesomorphous polypropylene webs, the blown microfiber web is preferably quenched by spraying with a liquid such as water or by cooling the collector drum onto which the microfiber web is collected. Optimum quenching can be achieved by spraying the fiber web near the die, then collecting the web on a cooled drum. The water spray is preferably at a temperature of less than about 50° F. (10° C.) and less than about 1 inch (2.5 cm) from the die and the collector drum is preferably about 2 in (5 cm) to 4 in (10 cm) from the die, but can be as much as 8 in (20 cm) to 10 in (25 cm) depending on extrusion rates.

The non-crystalline mesomorphous phase polypropylene can be irradiated by sterilizing ionizing radiation such as gamma radiation. The dosage of gamma radiation is generally in the range of about 2.5 to 4.0 Mrad for sterilization of medical articles.

The following non-limiting examples are provided to further illustrate the invention.

EXAMPLES 1-3 AND COMPARATIVE EXAMPLE 1

Polypropylene films were extruded from Gulf PX2252 polypropylene polymer (melt flow index: 300; average molecular weight, by GPC: 51,900) using a 1¼ in (3.2 cm) Brabender extruder with a 12 in (30.5 cm) wide film die at a thickness of about 1.5 mil (0.04 mm) under the following conditions:

| | |
|---|---|
| Melt temperature (°C): | 200 |
| Screw speed (rpm): | 30 |
| Polymer flow rate (kg/hr): | 5 |
| Die temperature (°C): | 204 |

The films were extruded onto a chrome-plated 3 in (7.6 cm) diameter casting roll spaced one inch (2.5 cm) from the die. The film was in contact with the roll for about 2.5 seconds. The roll was maintained at the temperatures indicated in Table 1. The percent crystallinity was determined for each film by measuring the density using a gradient column. The percent crystallinities are also shown in Table 1.

TABLE 1

| | Roll Temperature (°C) | Percent Crystallinity |
|---|---|---|
| Example 1 | 6.7 | 31.9 |
| Example 2 | 15.5 | 32.4 |
| Example 3 | 23.9 | 33.2 |
| Comparative Example 1 | 65.5 | 50.0 |

Figure 1:
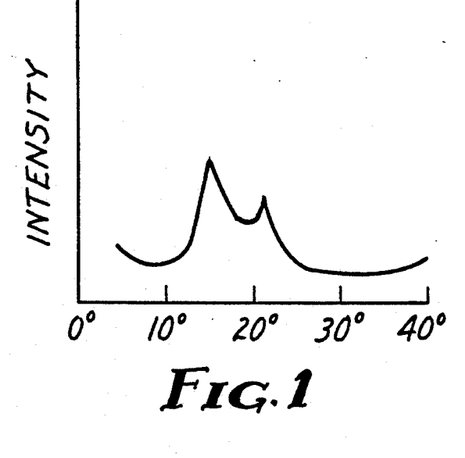
FIG. 1 is the X-ray diffraction pattern of the non-crystalline mesomorphous polypropylene film of Example 1.

Each film was analyzed using wide angle X-ray diffraction to determine the morphology of the film. FIGS. 1-3 show the X-ray diffraction curves for the films of Examples 1-3 respectively and are indicative of non-crystalline mesomorphous polypropylene. FIG. 4 shows the X-ray diffraction curve for the film of Comparative Example 1 and is indicative of crystalline polypropylene.

Samples of each film were irradiated with 1 Mrad gamma radiation and tested together with non-irradiated samples quenched at the same temperature for yield stress and elongation at break using ASTM Test Method D882-31 after periods of storage at 70° F. (22° C.). The results are shown in Table 2.

TABLE 2

| Example (Quench temp.) | Time (mo.) | Yield stress (kg/cm²) | Elongation at break (%) |
|---|---|---|---|
| Example 1 | 0 | 203 | >400 |
| (6.7° C.) | 0.5 | 196 | >400 |
| | 1 | 196 | >400 |
| | 2 | 188 | >400 |
| | 3 | 206 | >400 |
| | 6 | 209 | >400 |
| Non-irradiated | 0 | 203 | >400 |
| (6.7° C.) | 3 | 196 | >400 |
| Example 2 | 0 | 188 | >400 |
| (5.5° C.) | 0.5 | 181 | >400 |
| | 1 | 186 | >400 |
| | 2 | 191 | >400 |
| | 3 | 201 | >400 |
| | 6 | 195 | >400 |
| Non-irradiated | 0 | 188 | >400 |

TABLE 2-continued

| Example (Quench temp.) | Time (mo.) | Yield stress (kg/cm²) | Elongation at break (%) |
|---|---|---|---|
| (5.5° C.) | 3 | 185 | >400 |
| Example 3 | 0 | 192 | >400 |
| (23.9° C.) | 0.5 | 188 | >400 |
| | 1 | 203 | >400 |
| | 2 | 193 | >400 |
| | 3 | 209 | >400 |
| | 6 | 195 | >400 |
| Non-irradiated | 0 | 192 | >400 |
| (23.9° C.) | 3 | 199 | >400 |
| Comparative | 0 | 326 | 16 |
| Example 1 | 0.5 | 324 | 11 |
| (65.5° C.) | 1 | 331 | 13 |
| | 2 | 333 | 13 |
| | 3 | 333 | 11 |
| | 6 | 321 | 7 |
| Non-irradiated | 0 | 326 | 16 |
| (65.5° C.) | 3 | 342 | 19 |

Samples of each film were irradiated with 3 Mrad gamma radiation and tested as described hereinabove. The results are shown in Table 3.

TABLE 3

| Example (Quench temp.) | Time (mo) | Yield stress (kg/cm²) | Elongation at break (%) |
|---|---|---|---|
| Example 1 | 0 | 204 | >400 |
| (6.7° C.) | 0.5 | 202 | >400 |
| | 1 | 199 | >400 |
| | 2 | 203 | >400 |
| | 3 | 211 | >400 |
| | 6 | 209 | >360 |
| Non-irradiated | 0 | 204 | >400 |
| (6.7° C.) | 3 | 197 | >400 |
| Example 2 | 0 | 188 | >400 |
| (15.5° C.) | 0.5 | 194 | >400 |
| | 1 | 186 | >400 |
| | 2 | 192 | >400 |
| | 3 | 206 | >400 |
| | 6 | 195 | 335 |
| Non-irradiated | 0 | 188 | >400 |
| (15.5° C.) | 3 | 185 | >400 |
| Example 3 | 0 | 192 | >400 |
| (23.9° C.) | 0.5 | 195 | >400 |
| | 1 | 201 | >400 |
| | 2 | 199 | >400 |
| | 3 | 201 | >400 |
| | 6 | 188 | >00 |
| Non-irradiated | 0 | 192 | >400 |
| (23.9° C.) | 3 | 200 | >400 |
| Comparative | 0 | 326 | 16 |
| Example 1 | 0.5 | 314 | 9 |
| (65.5° C.) | 1 | 314 | 6 |
| | 2 | 312 | 7 |
| | 3 | too brittle to test | |
| | 6 | | |
| Non-irradiated | 0 | 326 | 16 |
| (65.5° C.) | 3 | 342 | 19 |

As can be sen from the data in Tables 2 and 3, the non-crystalline mesomorphous films of Examples 1-3 exhibited minimal degradation of tensile properties after irradiation with as much as a 3 Mrad sterilizing dose of gamma radiation even after storage periods of six months.

EXAMPLES 4-6 AND COMPARATIVE EXAMPLE 2

Polypropylene films were extruded from Exxon PP-3014 polypropylene polymer (melt flow index—12; average molecular weight, by GPC: 161,000) using a 1¼ in (3.2 cm) Brabender extruder with a 12 in (30.5 cm) wide film die at a thickness of about 1.5 mil (0.04 mm) under the following conditions:

| | |
|---|---|
| Melt temperature (°C.) | 203 |
| Screw speed (rpm) | 40 |
| Polymer flow rate (kg/hr) | 5 |
| Die temperature (°C.) | 204 |

The films were extruded onto a chrome-plated 3 in (7.6 cm) diameter casting roll spaced one inch (2.5 cm) from the die. The film was in contact with the roll for about 2.5 seconds. The roll was maintained at the temperature indicated in Table 4. The percent crystallinity was determined for each film by measuring the density using a gradient column. The percent crystallinities are also shown in Table 4.

TABLE 4

| | Roll temp. (°C.) | Percent crystallinity |
|---|---|---|
| Example 4 | 6.7 | 32.7 |
| Example 5 | 15.5 | 31.9 |
| Example 6 | 23.9 | 32.9 |
| Comparative Example 2 | 65.5 | 48.8 |

Figure 5:
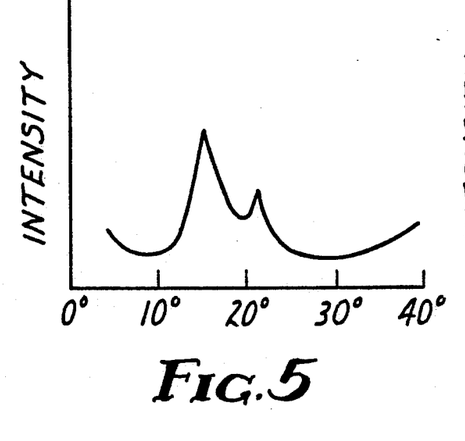
FIG. 5 is the X-ray diffraction pattern of the non-crystalline polypropylene film of Example 4.

Each film was analyzed using wide angle X-ray diffraction to determine the morphology of the film. FIGS. 5-7 show the X-ray diffraction curves for the films of Examples 4-6 respectively and are indicative of non-crystalline mesomorphous polypropylene. FIG. 8 shows the X-ray diffraction curve for the film of Comparative Example 2 and is indicative of crystalline polypropylene.

Samples of each film were irradiated with 3 Mrad gamma radiation and tested together with non-irradiated samples quenched at the same temperature for yield stress and elongation at break using ASTM Test Method D882-31 after periods of storage at 70° F. (22° C.). The results are shown in Table 5.

TABLE 5

| Example (Quench temp.) | Time (mo.) | Yield stress (kg/cm$^2$) | Elongation at break (%) |
|---|---|---|---|
| Example 4 (6.7° C.) | 0 | 203 | >400 |
| | 0.5 | 205 | >400 |
| | 1 | 220 | >400 |
| | 2 | 214 | >400 |
| | 3 | 218 | >400 |
| | 6 | 233 | >400 |
| Non-irradiated (6.7° C.) | 0 | 203 | >400 |
| | 3 | 213 | >400 |
| Example 5 (15.5° C.) | 0 | 205 | >400 |
| | 0.5 | 204 | >400 |
| | 1 | 221 | >400 |
| | 2 | 217 | >400 |
| | 3 | 223 | >400 |
| | 6 | 219 | >400 |
| Non-irradiated (15.5° C.) | 0 | 205 | >400 |
| | 3 | 211 | >400 |
| Example 6 (23.9° C.) | 0 | 209 | >400 |
| | 0.5 | 215 | >400 |
| | 1 | 231 | >400 |
| | 2 | 228 | >400 |
| | 3 | 224 | >400 |
| | 6 | 237 | >400 |
| Non-irradiated (23.9° C.) | 0 | 209 | >400 |
| | 3 | 220 | >400 |
| Comparative Example 2 (65.5° C.) | 0 | 322 | >400 |
| | 0.5 | 321 | 337 |
| | 1 | 335 | 320 |
| | 2 | 347 | 320 |
| | 3 | 340 | 250 |
| | 6 | 335 | 56 |
| Non-irradiated | 0 | 322 | >400 |
| (65.5° C.) | 3 | 343 | >400 |

As can be seen from the data in Table 5, the non-crystalline mesomorphous films of Examples 4-6 showed no degradation of tensile properties after irradiation with a 3 Mrad sterilizing dose of gamma radiation even after storage periods of six months. The film of Comparative Example 2, when irradiated with a 3 Mrad dose of gamma radiation, exhibited some degradation within 0.5 month and severe degradation after six months storage.

EXAMPLES 7-9 AND COMPARATIVE EXAMPLE 3

Polypropylene films were extruded from Arco 8670 polypropylene polymer (melt flow index - 4; average molecular weight, by GPC - 204,000) using a 1¼ in (3.2 cm) Brabender extruder with a 12 in (30.5 cm) wide film die at a thickness of about 1.5 mil (0.04 mm) under the following conditions:

| | |
|---|---|
| Melt temperature (°C.) | 206 |
| Screw speed (rpm) | 47 |
| Polymer flow rate (kg/hr) | 4.7 |
| Die temperature (°C.) | 204 |

The films were extruded onto a chrome-plated 3 in (7.6 cm) diameter casting roll spaced one inch (2.5 cm) from the die. The film was in contact with the roll for about 2.5 seconds. The roll was maintained at the temperature indicated in Table 6. The percent crystallinity was determined for each film by measuring the density using a gradient column. The percent crystallinities are also shown in Table 6.

TABLE 6

| | Roll temp. (°C.) | Percent crystallinity |
|---|---|---|
| Example 7 | 6.7 | 34.6 |
| Example 8 | 15.5 | 37.3 |
| Example 9 | 23.9 | 35.9 |
| Comparative Example 3 | 65.5 | 64.6 |

Figure 9:
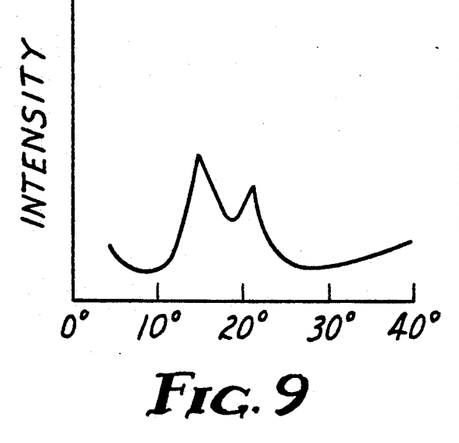
FIG. 9 is the X-ray diffraction pattern of the non-crystalline mesomorphous polypropylene film of Example 7.

Each was analyzed using wide angle X-ray diffraction to determine the morphology of the film. FIGS. 9-11 show the X-ray diffraction curves for the films of Examples 7-9 respectively and are indicative of non-crystalline mesomorphous polypropylene. FIG. 12 shows the X-ray diffraction curve for the film of Comparative Example 3 and is indicative of crystalline polypropylene.

Samples of each film were irradiated with 3 Mrad gamma radiation and tested together with non-irradiated samples quenched at the same temperature for yield stress and elongation at break using ASTM Test Method D882-31 after periods of storage at 70° F. (22° C.). The results are shown in Table 7.

TABLE 7

| Example (Quench temp.) | Time (mo) | Yield Stress (kg/cm$^2$) | Elongation at break (%) |
|---|---|---|---|
| Example 7 (6.7° C.) | 0 | 210 | >400 |
| | 0.5 | 214 | >400 |
| | 1 | 208 | >400 |
| | 2 | 203 | >400 |

TABLE 7-continued

| Example (Quench temp.) | Time (mo) | Yield Stress (kg/cm²) | Elongation at break (%) |
|---|---|---|---|
| | 3 | 222 | >400 |
| | 6 | 279 | >400 |
| Non-irradiated (6.7° C.) | 0 | 210 | >400 |
| | 3 | 213 | >400 |
| Example 8 (15.5° C.) | 0 | 209 | >400 |
| | 0.5 | 223 | >400 |
| | 1 | 226 | >400 |
| | 2 | 217 | >400 |
| | 3 | 225 | >400 |
| | 6 | 286 | >400 |
| Non-irradiated (15.5° C.) | 0 | 209 | >400 |
| | 3 | 221 | >400 |
| Example 9 (23.9° C.) | 0 | 222 | >400 |
| | 0.5 | 237 | >400 |
| | 1 | 226 | >400 |
| | 2 | 228 | >400 |
| | 3 | 237 | >400 |
| | 6 | 279 | >400 |
| Non-irradiated (23.9° C.) | 0 | 222 | >400 |
| | 3 | 231 | >400 |
| Comparative Example 3 (65.5° C.) | 0 | 306 | >400 |
| | 0.5 | 320 | >400 |
| | 1 | 315 | >400 |
| | 2 | 316 | >400 |
| | 3 | 319 | 350 |
| | 6 | 307 | 260 |
| Non-irradiated (65.5° C.) | 0 | 306 | >400 |
| | 3 | 329 | >400 |

EXAMPLE 10

A melt blown polypropylene microfiber web having a weight of 20 g/m² was extruded, as described in Wente, Van A., "Superfine Thermoplastic Fibers", supra, using Escorene PP 3085 polypropylene polymer (available from Exxon Chemical Americas.) The extruder conditions were:

| | |
|---|---|
| Polymer rate (kg/hr) | 6.5 |
| Polymer melt temperature (°C.) | 329 |
| Air temperature (°C.) | 343 |
| Air pressure (kPa) | 138 |

The fibers were quenched with water at a temperature of 40° F. (4° C.) and at a rate of 5 gal/hr (19 l/hr) with the spray located 6 inches (15 cm) below the die and directed at the fibers as they exited the die. The web was collected on a drum maintained at a temperature of 40° F. (4° C.), by dipping the roll in ice water, to further quench the web.

Figure 13:
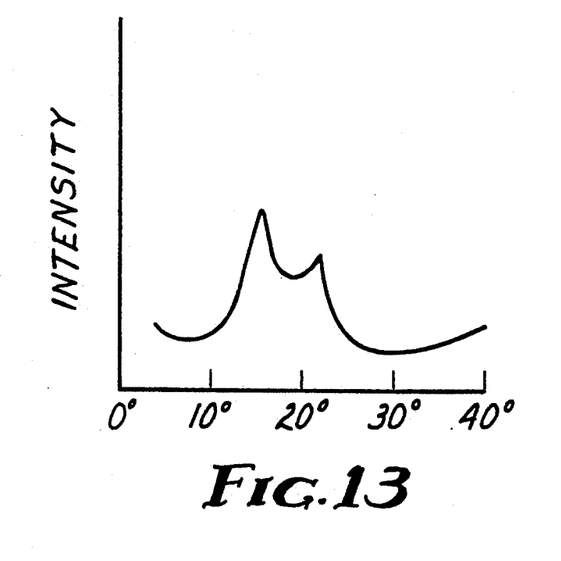
FIG. 13 is the X-ray diffraction pattern of the non-crystalline mesomorphous polypropylene blown microfiber web of Example 10.

The quenched web was analyzed by wide angle X-ray diffraction as shown in FIG. 13 and found to be non-crystalline mesomorphic in structure. The percent crystallinity of the web, as determined by density was found to be 33 percent.

Samples of the non-crystalline mesomorphic web were sterilized using gamma radiation at a dosage of between 2.86 to 3.39 Mrad. The sterilized non-crystalline mesomorphic web was tested for yield strength and elongation at break after various periods of storage using an Instron Tensile Tester with a 1 in (2.5 cm) wide by 5 in (12.7 cm) long sample at a rate of 5 in (12.7 cm) per minute. The results are shown in Table 10.

TABLE 10

| Time (days) | Yield stress (kg) | Elongation at break (%) |
|---|---|---|
| 0 (not sterilized) | 1.2 | 52 |
| 3 | 0.9 | 51 |
| 10 | 0.9 | 44 |
| 17 | 1.0 | 58 |
| 22 | 1.1 | 58 |

COMPARATIVE EXAMPLE 4

Melt blown polypropylene microfiber webs were prepared in a manner similar to that used in Example 10, except that the fibers were not water quenched. A first sample having a weight of 26.6 g/m² had a tensile strength of 0.63 kg when tested as in Example 12. A second sample having a weight of 26.4 g/m was sterilized using gamma radiation at a dosage of 2.5 Mrad. Two weeks after sterilization, this second sample had a tensile strength of 0.34 kg, a tensile strength reduction of 46%. After storage for an additional four weeks, the second sample had degraded to an extent that disintegration and powdering occurred on handling.

EXAMPLE 11 AND COMPARATIVE EXAMPLE 5

Melt blown microfiber web was extruded using Escorene PP 3145 polypropylene polymer (available from Exxon Chemical Americas) as in Example 10 with extruder conditions of:

| | |
|---|---|
| Polymer rate (kg/hr) | 4.5 |
| Polymer melt temperature (°C.) | 290 |
| Air temperature (°C.) | 292 |
| Air pressure (kPa) | 124 |

For Example 11, the fibers were quenched as in Example 10 to produce non-crystalline mesomorphic polypropylene web. For Comparative Example 5, the extruded fibers were not quenched, producing crystalline polypropylene web.

Samples of the non-crystalline mesomorphic polypropylene web and the crystalline polypropylene web were sterilized using gamma radiation at a dosage of about 3 Mrads.

Sterilized and unsterilized samples of the non-crystalline mesomorphic polypropylene and the crystalline polypropylene were tested for initial elongation at break and elongation at break after the intervals set forth in Table 11.

TABLE 11

| | Elongation at Break (%) | | | |
|---|---|---|---|---|
| | Example 11 | | Comparative Example 5 | |
| Time (days) | Not Sterilized | Sterilized | Not Sterilized | Sterilized |
| 0 | 50 | 45 | 20 | 21 |
| 13 | 38 | 24 | 15 | 7 |
| 21 | 35 | 37 | 15 | 7 |
| 28 | 34 | 35 | 14 | 9 |
| 35 | 36 | 26 | 13 | 7 |
| 42 | 36 | 40 | 11 | 9 |
| 52 | 31 | 28 | 10 | 7 |
| 67 | 36 | 26 | 12 | 6 |
| 83 | 34 | 31 | 13 | 8 |

As can be seen from the data in Table 11, the loss of tensile strength of the sterilized non-crystalline polypropylene (31%) was comparable to that of the non-sterilized non-crystalline polypropylene (32%) at an 83 day interval. In contrast, the sterilized crystalline polypropylene exhibited about double the loss in elongation as the non-sterilized crystalline polypropylene, the losses being 62% and 35% respectively.

Various modifications and alterations of this invention will be apparent to those skilled in the art without departing from the scope and spirit of this invention and this invention should not be restricted to that set forth herein for illustrative purposes.

We claim:

1. An radiation-sterlized polypropylene article consisting essentially of non-crystalline mesomorphic polypropylene which is substantially undegraded after at least six months storage.

2. The irradiated polypropylene article of claim 1 wherein the percent crystallinity of the non-crystalline mesomorphous polypropylene is below about 45 percent.

3. The irradiated polypropylene article of claim 1 wherein said article is a film.

4. The irradiated polypropylene article of claim 1 wherein said article is a blown microfiber web.

5. The irradiated polypropylene article of claim 1 further comprising antistatic materials, dyes, plasticizers, ultraviolet absorbers and nucleating agents.

6. A sterile pack comprising a gamma radiation sterilized polypropylene article consisting essentially of non-crystalline mesomorphic polypropylene contained within a sealed container, said article being substantially undegraded after six months storage.

7. The sterile pack of claim 6 wherein the percent crystallinity of the non-crystalline mesomorphous polypropylene is below about 45 percent.

8. The sterile pack of claim 6 wherein said non-crystalline mesomorphic polypropylene further comprises antistatic materials, dyes, plasticizers, ultraviolet absorbers and nucleating agents.

9. The polypropylene article of claim 1 wherein said non-crystalline polypropylene is defined by wide angle X-ray diffraction.

* * * * *